United States Patent [19]

Kauvar

[11] Patent Number: 5,133,866

[45] Date of Patent: * Jul. 28, 1992

[54] METHOD TO IDENTIFY ANALYTE-BENDING LIGANDS

[75] Inventor: Lawrence M. Kauvar, San Fransico, Calif.

[73] Assignee: Terrapin Technologies, Inc., San Francisco, Calif.

[ * ] Notice: The portion of the term of this patent subsequent to Oct. 16, 2007 has been disclaimed.

[21] Appl. No.: 429,721

[22] Filed: Oct. 31, 1989

Related U.S. Application Data

[63] Continuation-in-part of Ser. No. 355,042, May 16, 1989, Pat. No. 4,963,263, which is a continuation of Ser. No. 172,626, Mar. 24, 1988, abandoned, which is a continuation-in-part of Ser. No. 255,906, Oct. 11, 1988.

[51] Int. Cl.$^5$ .............................................. B01D 15/08
[52] U.S. Cl. .................... 210/635; 210/656; 436/161; 530/413
[58] Field of Search ............ 210/635, 656, 658, 198.2, 210/502.1; 502/400, 401, 402, 403, 404; 530/413; 436/161; 422/70

[56] References Cited

U.S. PATENT DOCUMENTS

| | | | |
|---|---|---|---|
| 4,125,492 | 11/1978 | Cuatrecasas et al. | 210/635 |
| 4,330,440 | 5/1982 | Ayers et al. | 210/635 |
| 4,334,972 | 6/1982 | Soderberg | 210/635 |
| 4,464,165 | 8/1984 | Pollard, Jr. | |
| 4,525,465 | 6/1985 | Someno et al. | 210/656 |
| 4,544,485 | 10/1985 | Pinkerton et al. | 210/502.1 |
| 4,612,121 | 9/1986 | Hermansson | 210/635 |
| 4,663,163 | 5/1987 | Hou et al. | 424/101 |
| 4,693,985 | 9/1987 | Degen et al. | 210/198.2 |
| 4,694,044 | 9/1987 | Kiniwa | 210/635 |

FOREIGN PATENT DOCUMENTS

| | | | |
|---|---|---|---|
| 62-278450 | 12/1987 | Japan | 210/198.2 |
| 62-278451 | 12/1987 | Japan | 210/198.2 |
| 8600991 | 2/1986 | PCT Int'l Appl. | 210/198.2 |
| 8606487 | 11/1986 | PCT Int'l Appl. | 210/198.2 |

OTHER PUBLICATIONS

May, *Separation and Purification*, 3rd edition, 1978, (Edmond S. Perry, et al., eds.), vol. 12, "Techniques of Chemistry" (New York: John Wiley, publishers), pp. 257-293.
Peterson et al., (1984) "Displacement Chromatography of Proteins" *Methods in Enzymology* 104:113—133.
Armstrong et al., (1984) "Cyclodextrin Bonded Phases for LC Separation" *J. Chromatographic Science* 22:411–415.
Atassi et al., (1977), "Canan Antibody-Combining Site be Mimicked Synthetically?" *J. Biological Chemistry* 252(24):8784–8787.
McCormick et al., (1984) "Localization and Synthesis of Acetylcholine-Binding Site" *Biochem. J.* 224:995–1000.
Seiden et al., (1986) "Hypervariable Region Peptides"*J. Immunology* 136(2):582–587.
Roux et al., (1987) "Construction of an Extended Three Dimensional Iditope map" *Proc. Natl. Acad. Sci. (USA)* 84:4984–4988.
Geysen et al., (1984) "Use of Peptide Synthesis" *Proc. Natl. Acad. Sci. (USA)* 81:3998–4002.
Houghten, (1985) "General Method for the Rapid Solid Phase Synthesis of Peptides" *Proc. Natl. Acad. Sci. (USA)* 82:5131–5135.
Takeo et al., (1978) "Binding Constants of Dextrans and Isomaltose" *Journal of Immunology* 121(6):2305–2310.
Varga et al., (1974) "Immunglobulins with Multiple Binding Functions" *Journal of Immunology* 112(4): 1565–1570.
Janin, (1979) "Surface and Inside Volumes in Globular Proteins" *Nature* 277:491–492.
Eisenberg et al., "The Hydrohobic Moment Detects Periodicity" *Proc. Natl. Acad. Sci. (USA)* 81:140–144.
Eisenberg et al., (1982), "The Helican Hydrophobic Moment" *Nature* 299:371–374.

*Primary Examiner*—Ernest G. Therkorn
*Attorney, Agent, or Firm*—Irell & Manella

[57] ABSTRACT

The invention provides methods to obtain specific paralogs which are capable of specifically binding a selected moiety. Such paralogs are useful for chromatographic separations and purifications of desired analytes and in binding assays such as immunoassays involving said analytes, as well as for any purpose which requires said specific binding. The invention also provides kits for these determinations, and methods to synthesize panels of candidate paralogs.

30 Claims, 11 Drawing Sheets

AFFINITY (BINDING) OF ANALYTE

← PARALOGS →

BINDING OF MIXTURE

← PARALOGS →

BINDING OF MIXTURE IN PRESENCE OF ANALYTE

← PARALOGS →

|     | N-term | 5 | 4 | 3 | C-term |     | N-term | 5 | 4 | 3 | C-term |
| --- | --- | --- | --- | --- | --- | --- | --- | --- | --- | --- | --- |
| 1.  | V | A | V | F | A | 49. | G | S | S | S | F |
| 2.  | F | G | W | A | I | 50. | G | W | G | K | W |
| 3.  | G | A | V | V | F | 51. | W | G | D | G | P |
| 4.  | V | V | I | A | P | 52. | N | S | W | G | A |
| 5.  | A | A | A | F | F | 53. | S | H | P | G | W |
| 6.  | M | V | V | G | W | 54. | S | D | A | A | A |
| 7.  | I | G | G | V | A | 55. | A | N | H | A | A |
| 8.  | G | F | W | W | M | 56. | D | P | W | S | W |
| 9.  | S | I | P | F | I | 57. | W | H | G | P | H |
| 10. | W | V | G | W | A | 58. | S | G | D | P | V |
| 11. | G | P | G | I | F | 59. | H | P | H | G | M |
| 12. | A | F | V | W | S | 60. | S | S | H | A | G |
| 13. | N | V | W | P | W | 61. | G | P | K | A | A |
| 14. | W | I | G | S | W | 62. | H | H | G | S | W |
| 15. | G | A | G | G | F | 63. | A | N | S | S | W |
| 16. | G | M | W | G | W | 64. | S | M | D | S | W |
| 17. | F | V | A | S | G | 65. | A | D | A | N | A |
| 18. | W | G | A | V | P | 66. | G | W | S | D | A |
| 19. | A | S | M | I | A | 67. | N | H | P | G | G |
| 20. | V | A | V | G | S | 68. | M | G | K | A | H |
| 21. | V | F | S | S | V | 69. | N | D | M | S | W |
| 22. | M | W | V | H | W | 70. | A | N | K | M | G |
| 23. | S | V | A | F | P | 71. | G | W | S | N | D |
| 24. | S | A | M | W | W | 72. | G | D | P | D | G |
| 25. | A | W | V | G | H | 73. | H | A | A | N | D |
| 26. | F | W | W | P | H | 74. | S | K | S | G | G |
| 27. | A | M | S | A | W | 75. | D | W | S | W | K |
| 28. | W | A | V | P | S | 76. | A | D | H | N | G |
| 29. | P | G | G | G | W | 77. | G | D | S | G | D |
| 30. | W | W | S | V | S | 78. | S | H | D | P | P |
| 31. | V | D | W | A | A | 79. | P | S | H | K | M |
| 32. | S | G | W | G | M | 80. | S | A | G | D | K |
| 33. | S | W | H | W | G | 81. | D | P | N | A | D |
| 34. | M | W | S | G | P | 82. | M | H | D | S | P |
| 35. | W | A | P | G | S | 83. | P | S | D | D | N |
| 36. | W | D | W | A | G | 84. | D | A | S | D | H |
| 37. | A | I | S | P | S | 85. | H | D | D | S | S |
| 38. | W | S | A | G | W | 86. | G | K | M | D | K |
| 39. | G | S | G | F | H | 87. | D | A | K | S | D |
| 40. | A | A | A | A | S | 88. | S | S | H | D | K |
| 41. | S | S | P | S | A | 89. | S | K | F | W | Y |
| 42. | G | W | S | G | S | 90. | P | L | A | Q | G |
| 43. | W | M | H | S | G | 91. | P | L | A | Q | G |
| 44. | A | S | G | H | W | 92. | G | L | A | Q | G |
| 45. | N | G | M | G | G | 93. | G | L | A | Q | K |
| 46. | W | G | N | P | M | 94. | S | V | N | M | K |
| 47. | P | P | A | S | G | 95. | I | A | H | W | D |
| 48. | G | H | A | S | A | 96. | F | P | K | V | D |

FIG. 7

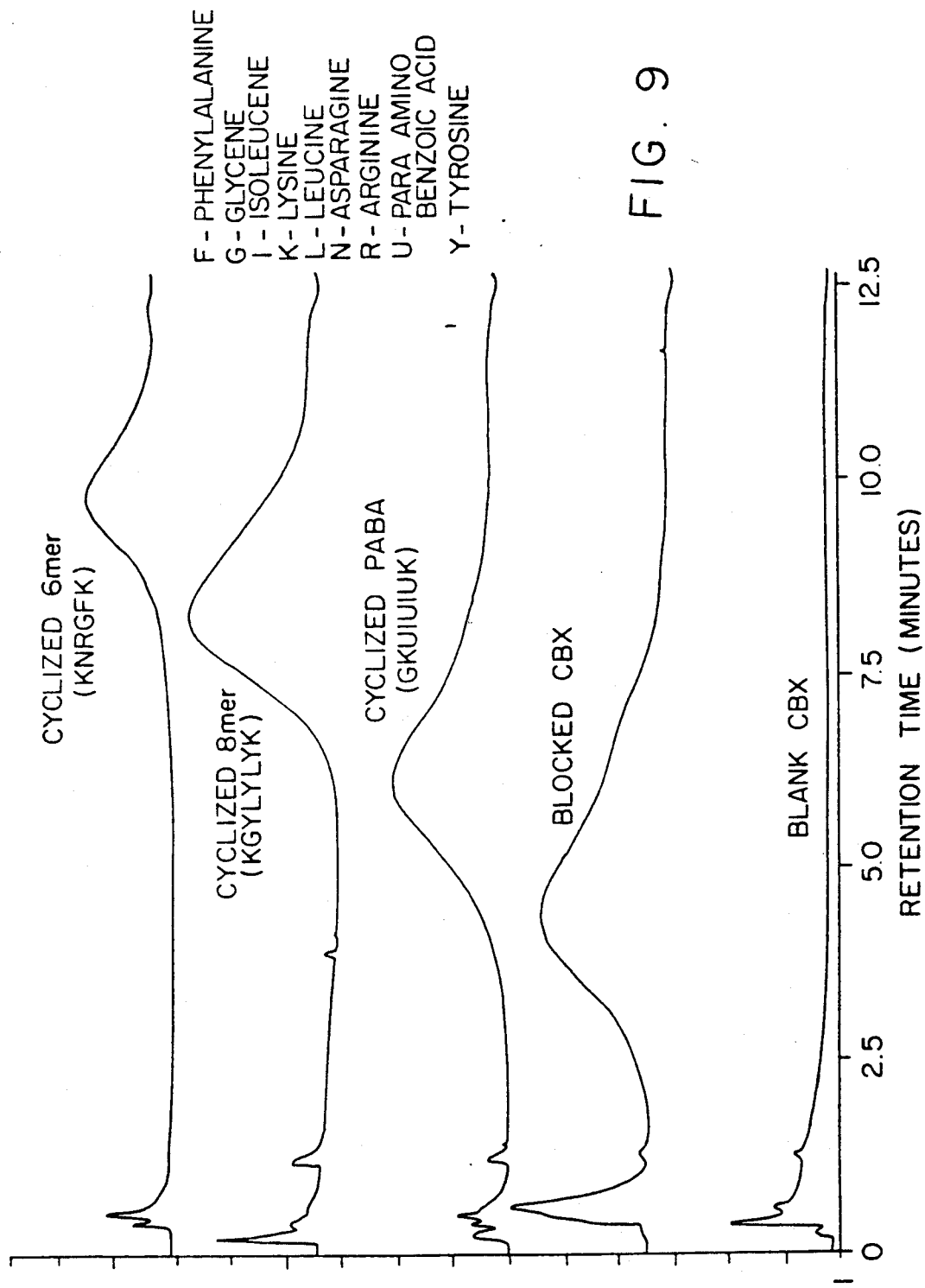

```
dna2 is a BASIC program written on contract for Terrapin
Technologies, Inc. by Stuart Ambler 29 Sept. 1989 dna2 output file, 10-10-1989 09:08:24
sequence seqlen  20
random number seed -4 intervals chosen by operator at run time:
   G+C percent
low  = 1      20  to  30 %
high = 2      70  to  80 %
   number of G+C percent regions
low  = 1       1  to   2 regions
high = 2       4  to   5 regions
   amount of direct symmetry
low  = 1       0  to   3  bases long
high = 2       5  to  10 bases long
   amount of complementary strand (dyad) symmetry
low  = 1       0  to   4 bases long
high = 2       5  to  10 bases long 16 out of 16 bins were filled in this run. Bin contents
follow. The sequence is listed on the first line; the sequence
with G and C replaced by 1, and A and T replaced by 0, is printed
on a second line; the sequence with regions indicated by
successive 1's, 2's, etc. printed on a third line; the sequence
with the longest symmetry showing and other bases replaced by X
is printed on a fourth line; and the sequence with the longest
complementary symmetry showing and other bases replaced by X is
printed on a fifth line.
```

|                  | per cent GC | # of regions | direct symmetry | dyad symmetry |
|------------------|-------------|--------------|-----------------|---------------|
| bin description  |             |              |                 |               |
| ................ | ........... | ............ | ............... | ............. |
| bin number       | 1           | 1            | 1               | 1             |
| bin properties   | 30          | 2            | 3               | 0             |

```
GATTATTACTTTGGATGTAG
10000000100011001001
11111111111122222222
xATTxTTAxxxxxxxxxxxx
xxxxxxxxxxxxxxxxxxxx
```

|                  | | | | |
|------------------|---|---|---|---|
| ................ | ........... | ............ | ............... | ............. |
| bin number       | 1 | 1 | 1 | 2 |
| bin properties   | 25 | 2 | 3 | 8 |

```
TAAGTTATCTATAACTTAGG
00010001000000100011
11111111111111112222
xxxxxTATxTATxxxxxxxx
TAAGTTATxxATAACTTAxx
```

FIG. 10-1

```
               per cent   # of      direct    dyad
bin description   GC     regions  symmetry  symmetry
..............................................................
bin number         1        1        2         1
bin properties    20        2        5         0

ATAGGATTAAGTAATTTTG
00011000000100000001
11111222222222222222
xxxxxxTTTAAxxAATTTxx
xxxxxxxxxxxxxxxxxxxx ..............................................................
bin number         1        1        2         2
bin properties    30        1        5         5

CAATGATTGTAACATTGAGA
10001000100010001010
11111111111111111111
CAATGxxxGTAACxxxxxxx
CAATGxxxxxxxCATTGxxx ..............................................................
bin number         1        2        1         1
bin properties    30        4        0         0

ATCATTCAGGTATACTTGTA
00100010110000100100
11111122223333444444
xxxxxxxxxxxxxxxxxxxx
xxxxxxxxxxxxxxxxxxxx ..............................................................
bin number         1        2        1         2
bin properties    25        4        3         5

ATACCTAAATAGACGATTTA
00011000000101100000
11111222222333344444
xxxxxxxxxTAGxxGATxxx
xxxxxTAAATxxxxxATTTA ..............................................................
bin number         1        2        2         1
bin properties    30        4        5         0

ATTCAACTACTAATCATTCC
00010010010000100011
11111122223333334444
xxxxxxxTACTAATCATxxx
xxxxxxxxxxxxxxxxxxxx
```

FIG. 10-2

| bin description | per cent GC | # of regions | direct symmetry | dyad symmetry |
|---|---|---|---|---|
| bin number | 1 | 2 | 2 | 2 |
| bin properties | 25 | 4 | 5 | 6 |

```
AAAATCAGGATTTTAGGTAT
00000101100000011000
11111222233333344444
xxxxxxxGGATTTTAGGxxx
AAAATCxxGATTTTxxxxxx
```

| bin description | per cent GC | # of regions | direct symmetry | dyad symmetry |
|---|---|---|---|---|
| bin number | 2 | 1 | 1 | 1 |
| bin properties | 70 | 2 | 3 | 0 |

```
TTCACGGTGGCGCAGGCCCT
00101110111110111110
11112222222222222222
xxxxCGGxGGCxxxxxxxxx
xxxxxxxxxxxxxxxxxxxx
```

| bin description | per cent GC | # of regions | direct symmetry | dyad symmetry |
|---|---|---|---|---|
| bin number | 2 | 1 | 1 | 2 |
| bin properties | 80 | 2 | 3 | 5 |

```
ACCCCGGGGCTAGCCCCTCG
01111111110011111011
11111111112222222222
xxxxCGGGGCxxxxxxxxxx
xxxxxGGGGCxxGCCCCxxx
```

| bin description | per cent GC | # of regions | direct symmetry | dyad symmetry |
|---|---|---|---|---|
| bin number | 2 | 1 | 2 | 1 |
| bin properties | 80 | 2 | 5 | 0 |

```
TCCACCCTGCCGGCCCCGTC
01101110111111111101
11111111222222222222
xxxxxxCTGCCxxxxCCGTC
xxxxxxxxxxxxxxxxxxxx
```

| bin description | per cent GC | # of regions | direct symmetry | dyad symmetry |
|---|---|---|---|---|
| bin number | 2 | 1 | 2 | 2 |
| bin properties | 80 | 2 | 5 | 5 |

```
CCGGTCCCGTGGCCGGACCA
11110111101111110110
11111111111111112222
CCGGTxxxxTGGCCxxxxxx
xxGGTCCxxxxxxxxGGACCx
```

FIG. 10-3

|                 | per cent GC | # of regions | direct symmetry | dyad symmetry |
|-----------------|-------------|--------------|-----------------|---------------|
| bin number      | 2           | 2            | 1               | 1             |
| bin properties  | 70          | 4            | 3               | 0             |

```
TCCTGCCTCGGCACTTCCCG
01101110111101001111
11111111222233334444
TCCxxCCTxxxxxxxxxxxx
xxxxxxxxxxxxxxxxxxxx
```

|                 | | | | |
|-----------------|---|---|---|---|
| bin number      | 2 | 2 | 1 | 2 |
| bin properties  | 70| 5 | 2 | 5 |

```
CCGGAACGCGCGATATCCGG
11110011111100001111
11112222333344445555
xxxxxxCGxGCxxxxxxxxx
CCGGAxxxxxxxxxxTCCGG
```

|                 | | | | |
|-----------------|---|---|---|---|
| bin number      | 2 | 2 | 2 | 1 |
| bin properties  | 75| 4 | 5 | 0 |

```
AGAGTGCGGGTCAGGGCGGG
01010111110101111111
11111222223333444444
xxxxxGCGGGxxxGGGCGxx
xxxxxxxxxxxxxxxxxxxx
```

|                 | | | | |
|-----------------|---|---|---|---|
| bin number      | 2 | 2 | 2 | 2 |
| bin properties  | 70| 4 | 5 | 5 |

```
ACTGGCGCACAACGCGCCCT
01011111010011111110
11112222333344444444
xxxxGCGCAxxACGCGxxxx
xxxGGCGCxxxxxGCGCCxx
```

FIG. 10-4

METHOD TO IDENTIFY ANALYTE-BENDING LIGANDS

CROSS-REFERENCE TO RELATED APPLICATION

This application is a continuation-in-part of U.S. Ser. No. 355,042 filed May 16, 1989, now U.S. Pat. No. 4,963,263, which is a file wrapper continuation of U.S. Ser. No. 172,626 filed Mar. 24, 1988, now abandoned, and is a continuation-in-part of pending U.S. Ser. No. 255,906, filed Oct. 11, 1988.

TECHNICAL FIELD

The invention relates to selection of specific binding moieties which can, for example, be used as chromatographic and analytical affinity ligands for specific analytes. More particularly, it concerns use of ligands selected from diverse sets of low molecular weight ($<7.5$ kd) "paralogs" of varying properties as affinity ligands which are useful in diagnosis and therapy, and in chromatographic techniques for detection and purification of a variety of analytes, in particular toxic contaminants of low immunogenicity, and in binding assays, such as immunoassays.

BACKGROUND ART

The paralogs prepared by the method of the invention are particularly useful in chromatographic applications. Two major developments in the practice of such chromatographic separations have been of dramatic importance over the last decade or so in facilitating the isolation of natural products, separation of components of mixtures, and analysis of complex compositions. These are the proliferation of the variety of available ligands such as specific antibodies for affinity chromatography, wherein the separation or analysis depends on a large difference in binding properties resulting from the specific interaction between a supported ligand and a desired analyte, and the advent of high performance liquid chromatography (HPLC) which permits rapid and efficient separation of multiple components through repetitive partitioning depending on small differences in their binding to a sorbent. These developments have overlapped only to a limited extent, as HPLC generally utilizes conditions which are inimical to many of the ligands used as specific affinity partners. The most common affinity partner for use in these techniques with respect to a spectrum of possible analytes has been a specific immunoglobulin or an immunoreactive fragment thereof. In general, this type of ligand is unstable with respect to the conditions employed in HPLC. HPLC often employs nonaqueous solvents, which are denaturing to many affinity ligands and the high pressures employed are also destructive to many of these substances.

In affinity based chromatography, a variety of solid supports and of affinity ligands can be used, as summarized in an early review article by May, S. W. in *Separation and Purification* 3rd Ed. (1978) Edmond S. Perry, et al, ed., vol. 12 in Techniques of Chemistry (J. Wiley). This review describes suitable supports for affinity chromatography emphasizing polysaccharide supports in addition to polyacrylamide gels, mixed gels, and various glasses and silica derivatives. Of these, only silica derivatives have gained wide acceptance for use in HPLC. However, the extent of derivatization of the support to modify its binding characteristics has been limited to altering hydrophobicity by conjugation of various hydrocarbon ligands or other simple molecules.

The present invention enables a convenient crossover between the HPLC and affinity approaches by providing a method to obtain ligands which have the required affinity specific for a selected member of an array of possible analytes as well as capability to withstand the conditions of HPLC. By providing maximal diversity in the choice of these ligands, there is made available an appropriate ligand to effect the desired separation in any arbitrary instance.

Others have attempted the crossover between HPLC and affinity chromatography in various ways. Peterson, E. A. et al *Meth Enz* (1984) 104:113-133 describe "displacement" chromatography wherein competition for the adsorption sites between adsorbed components is substituted for competition with eluant. Chromatographic supports which employ carbohydrates, such as cyclodextrins, with differential specific affinities for the substances to be separated have also been reported (Armstrong, D. W. et al *J Chrom Sci* (1984) 22:411-415).

An example of the ligands employed in the invention method are diverse sets of peptides of 4-20 amino acids, which are one form of the materials designated "paralogs" herein. A paralog mimics the portion of an immunoglobulin which specifically binds to the antigenic determinant or epitope of the antigen to which the antibody is raised. The segment complementary to this epitope is commonly designated a paratope, and since a peptide sequence in the paralog need not be the same as that occurring in the raised antibodies, the term paralog (or paratope analog) is used.

Synthesis of, and identification of, peptides which putatively are complementary to specific moieties has been done previously to a very limited extent. Atassi, M. Z., et al *J Biol Chem* (1977) 252:8784-8787 described the specific design of a peptide complementary to the antigenic sites of lysozyme. Knowledge of the three-dimensional contours of lysozyme permitted the synthesis of a peptide of dimensions and electron density patterns analogous to the deduced determinant. The putatively complementary peptide was obtained by preparing a sequence deliberately complementary in dimension and electron distribution to the determinant-mimicking peptide. The pseudo "paratope" peptides inhibited the reaction of lysozyme with antisera and specifically bound lysozyme to the exclusion of myoglobin or antibody. However, this property was later shown to be shared, and, in fact, exceeded by the peptide to which this "paratope" was a complement. Later work from the same group resulted in the synthesis of a peptide representing the acetyl choline binding site of a specific receptor and of a binding site in trypsin (McCormick, D. J., et al Biochem J (1984) 224:995-1000; Atassi, M. Z. *Biochem J* (1985) 226:477-485). The paratope or receptor or enzyme binding site-mimicking peptides were based on known structural parameters associated either with the antigenic determinant or with the determinant binding moiety.

In a different approach to defining binding sites at atomic resolution, recent work has shown that the idiotypic surface of antibodies can be mapped and peptides mimicking portions of this surface can be prepared. Contrary to expectation from Jerne's hypothesis, however, the idiotypes and paratopes do not precisely coincide. Seiden, M. V. *Am Assoc Immunol* (1986)

136:582-587; Roux, K. H. et al *Proc Natl Acad Sci USA* (1987) 84:4984-4988.

Recently, methods to mimic epitopes as specifically binding complementary components without knowledge of the characteristics of the specific interaction have been disclosed. The most relevant work is that of Geysen, H. M. at the Commonwealth Serum Laboratories in Australia. Geysen has devised an empirical method for preparing a panel of multiple candidate sequences whose ability to bind specifically to antibody can be empirically tested. In the Geysen approach, each of the candidate peptides is separately synthesized on an individual polyethylene support rod in relatively small amount. The support rods are arranged conveniently so as to dip individually into the wells of a microtitre tray. Typically 96 separate peptides can be simultaneously synthesized (the number corresponding to the arrangement of commercially available trays) The 96 peptides can also be simultaneously assayed for binding to antibodies or receptors using standard radioimmunoassay or ELISA techniques (See, for example, *Proc Natl Acad Sci* (USA) (1984) 81:3998-4002, PCT applications WO86/00991 and WO86/06487.)

A variety of candidate peptides can also be simultaneously synthesized in separate containers using the T-bag method of Houghten, R., *Proc Natl Acad Sci* (USA) (1985) 82:5131-5135.

Methods are also available for synthesis of alternate, nonpeptide, forms of candidate paralogs in multiple diverse sets. Thus, any moiety which is a composite molecule synthesized from a multiplicity of monomer units with varying properties, which monomer units can be varied across the members of a panel and can form the basis for the set of candidate paralogs.

These and other elements of the synthetic art can be productively used as a resource to construct the ligands needed for the conduct of the methods of the herein invention, and for uses such as for the preparation of chromatographic substrates or other specific binding applications.

DISCLOSURE OF THE INVENTION

The invention makes possible the systematic and facile selection of a substance capable of specific binding to any selected moiety. In one application, the invention provides a useful form of analytical and preparative chromatography on solid supports which permits a combination of the advantages of affinity chromatography and HPLC. By selecting and constructing appropriate substrates for chromatographic separations and purifications based on affinity, these procedures can be carried out under efficient conditions which permit ready analysis of components, or their purification or their removal from mixtures. Such techniques are particularly useful in removing toxic wastes from effluents, in assaying the quantity of toxins in reservoirs, in analysis of levels of materials at low concentration in the presence of a high concentration of irrelevant contaminants, and in preparative procedures involving HPLC. The invention permits this efficient use of chromatographic techniques by using effective means to ascertain appropriate paralog ligands for particular purification and separation problems, or for a desired binding assay. However, the invention method can provide a specifically binding paralog useful in a variety of contexts, including diagnosis and therapy.

Thus, in one aspect, the invention is directed to methods to obtain paralogs having specific affinity for a specified moiety, such as an analyte. The method of the invention comprises screening, for ability to selectively bind said moiety, a panel of individual candidate paralogs wherein said candidate paralogs have systematically varied values of at least two parameters which determine the ability of the paralog to bind other substances. Systematic variation in properties greatly reduces the number of candidates that need to be screened thus providing a significant advance over prior methods. Such screening may be done by individually testing each member of the panel with the moiety to be bound, or by means of kits which provide multiple test portions for simultaneous screening of the candidates. The candidate paralogs can be prepared by synthesizing the polymeric composite paralog moieties from monomer components in a manner predetermined to maximize the diversity of the parameters or may be prepared by synthesizing a random mixture of such paralogs and isolating diverse candidates by binding to and elution from a maximally diverse set of complementary ligands. In other aspects, the invention is directed to kits suitable for screening the paralog panels.

As mentioned above, in addition to chromatographic applications, the individual paralogs of correct specificity can be used as substitutes for antibodies or fragments thereof in immunoassay procedures. The paralogs may also be used instead of antibodies to screen mimotope panels for members capable of substituting for a particular hapten in the method of pseudo-idiotypic network (PIN) profiling described in U.S. Serial No. 108,130, assigned to the same assignee and incorporated herein by reference. The specifically binding paralogs are also useful in contexts wherein the moiety to be bound is a receptor, such as in therapy.

BRIEF DESCRIPTION OF THE DRAWINGS

FIG. 7 shows the panel of 90 candidate pentapeptide paralogs synthesized according to Example 1.

FIG. 9 shows the effect of cyclization of peptides on their behavior as chromatographic substrates for DDD.

FIGS. 10-1, 10-2, 10-3, and 10-4 show a panel of diverse DNA sequences designed by computer.

MODES OF CARRYING OUT THE INVENTION

Figure 1:
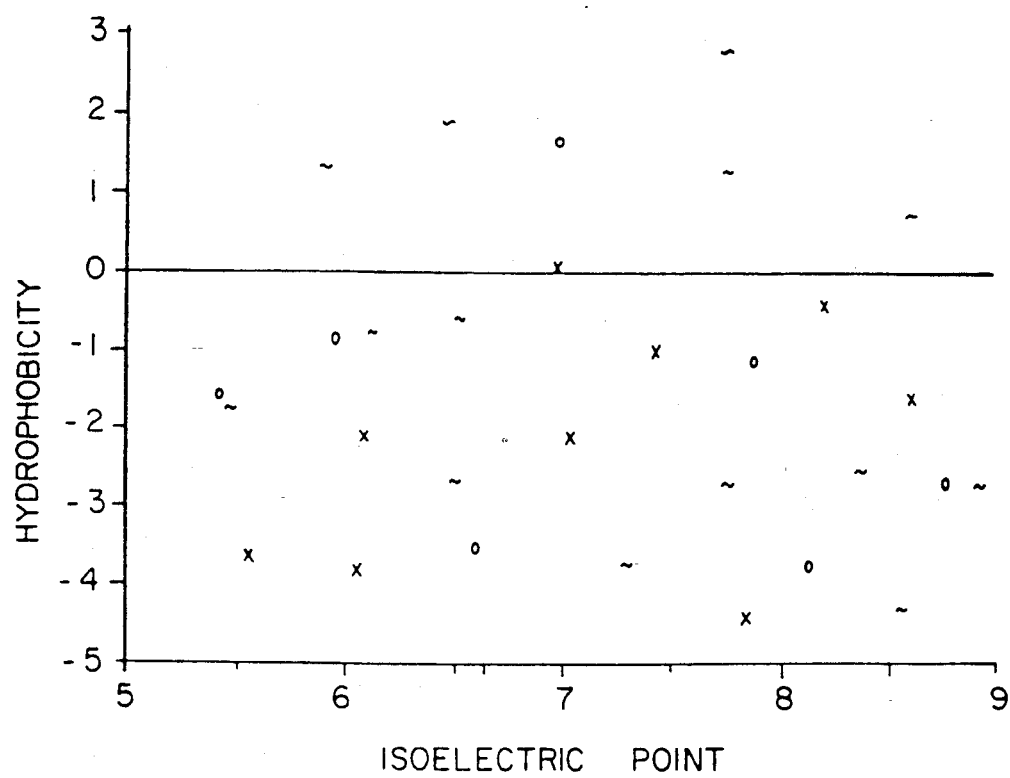
FIG. 1 shows the characteristics of a diverse set of 30 peptides generated by a FORTRAN program.

As used herein, "paralog" refers to a short "polymer" of MW <7500, or preferably <5000, more preferably <1000, composed of monomer units, which polymer has specific affinity for a specified moiety, such as an analyte or hapten. This "polymer" responsible for the affinity may, of course, be included in a larger molecule or conjugated to a solid support, and may be supplied as tandem copies. For selection by the screening method of the invention, an individual paralog is originally synthesized as a member of a panel of candidate paralogs which have maximized diversity with respect to at least two parameters which affect the ability of the paralog to bind to another substance. Therefore, the paralogs of the invention must be, in order to permit rational synthesis of the panel, composed of individual monomer units which monomer units can be varied across the members of the panel in a combinatorial fashion, thus generating the necessary superabundant diversity in a preparation. The diversity can be obtained by systematic variation of parameters through the design of synthesis of individual panel members, or may be achieved by the synthesis of random mixtures, depending on the approach to the formulation of the panel.

The resultant paralogs are "polymers", but need not be, and indeed cannot be, homopolymers such as polyethylene or polypropylene, and need not even be pseudohomopolymers—i.e., composed of monomeric units where the same type of linkage is employed to conjugate the monomeric units, such as is the case for peptides or nucleic acids, where individual monomers may vary but the basic linkage remains the same. A wide variety of such composite polymeric molecules may be used as members of the paralog panel of the invention, as will further be described below, but all share the characteristic of permitting synthesis of vastly more candidates than can be practically screened, thus creating a need for systematic methods of design and preparation of a diverse subset as provided by the invention.

The nature of the advantage of moieties composed of monomer units is seen, for example, in the case of peptides. If paralogs containing 6 amino acids in their primary sequence are employed, there are 64 million possible 6-mers using only the 20 naturally occurring amino acids. Of course, the synthesis of peptides need not be limited to these naturally occurring subunits, and the D-forms of the encoded amino acids as well as various nonencoded amino acids such as beta alanine, aminobutyric acid, citrulline, and the like can also be used. Hundreds of such non-encoded amino acids are known. Indeed, these may be preferred as they are expected to be more stable than the "natural" amino acids which are metabolites for microorganisms.

Paralogs provide spatial conformation and electron distribution patterns which are comparable in diversity to that generated by the immune system. While the paralog can be conceptualized in this manner as an antibody mimic it is, of course, not necessary that administration of the moiety to be bound, in fact, in every instance (or in any instance) raise immunoglobulins with a paratope of precisely the conformation and pattern of the paralog. It is sufficient that the paralog is capable of exhibiting analogous specific affinity properties with respect to the selected moiety.

"Specific affinity" refers to the ability of the paralog to bind to the selected moiety specifically—i.e., the strength of the interaction between this moiety and paralog is effectively greater than the strength of the interaction between the paralog and other materials which might be present with the selected moiety, so that binding to the paralog can be used to distinguish between for example, an analyte and a contaminant. Typical values for the specific affinity are of the order of $10^3$ l/mole to $10^4$ l/mole at a minimum, and are preferably or $10^8$ or $10^{10}$ l/mole. The needed value is dependent on the environment in which the selected moiety is found, and on the relative binding strength of the accompanying materials as well as their concentration. In some contexts, a lower affinity is quite adequate, or even preferable, for subsequent ease in elution, whereas if the paralog also binds strongly to the accompanying materials, especially those present in high concentration, a higher affinity may be required in order to set the binding of the selected moiety apart from that of these materials. In short, it is the relative affinity for the selected moiety in comparison with that for accompanying materials that is critical. However, the specific affinity should preferably result from the combined charge/spatial array characteristic of the paralog as complementary to the selected moiety, rather than entirely from a single generalized property such as pI or hydrophobic index.

Assessment of binding affinity of the selected moiety with a paralog can be made taking advantage of standard immunological methods. Methods to measure the affinity of interaction between antigens and high-affinity antibodies is standard; that of interaction with low-affinity antibodies can be measured as described, for example, Takeo, K., et al, *J Immunol* (1978) 121:2305–2310. Takeo et al describe measurement of binding constants of certain oligosaccharides to specific myeloma proteins using polyacrylamide gel electrophoresis and varying the nature and content of the oligosaccharides in the gel when determining mobilities of the proteins. The method is said to be useful in obtaining binding constants ranging from $10^2$–$10^6$ liters per mole. Varga, J. M., et al, *J Immunol* (1974) 112:1565–1570, describe the determination of binding constants across a comparable range using nylon-polystyrene whisker discs coupled by glutaraldehyde to immunoglobulins to test the binding of radioactive ligands. Thus, there are a number of protocols in addition to the currently used standard dilution immunoassay procedures in microtiter wells to evaluate binding and quantitate binding constants.

The invention provides means to screen panels to obtain paralogs which have specific affinity for a wide variety of selected moieties which may or may not be immunogenic. In addition to moieties which are themselves peptides, and which therefore may permit direct design of individual paralogs by the "complementarity" approach with regard to sequential overlapping portions of the primary amino acid sequence (a combination of the synthesis/analysis method of Geysen with the complementarity design approach of Atassi) the moieties to be bound may be of any origin including drugs such as penicillin, tetracycline, steroids, naproxen, theophylline, vitamins, such as vitamins K, D and A, various toxins such as PCBs, dioxin, and tetrabromoethylene, and any miscellaneous chemical substance having a defined molecular conformation or shape under specified conditions. Using the method of the invention, a specific peptide paralog can be found for virtually any type of moiety or a defined region thereof.

The obtention of the paralog for selected moieties, whether peptides or nonpeptides, can be approached by a screening procedure among candidate paralog peptides. In this approach, a panel of candidate paralogs having maximally diverse values for at least two parameters related to ability to bind other substances is prepared for screening. The panel is thus designed to cover a wide range of electron cloud pattern alternatives so that an approximation of the desired paralog can be obtained. Subsequent candidates within that range can be further tested for fine tuning.

In order to cover the range of electron cloud patterns which determine, it is understood, the ability of the paralog to bind to other substances, at least two parameters must be varied over more or less a maximal range. By "variation over a maximal range" is meant that the parameter has values which cover the useful range of values ordinarily found for this parameter, which range may be dependent on the context. For example, the isoelectric point, pI, ordinarily would vary over a range of about 2-12; theoretical values beyond these limits can certainly be postulated, but as a practical matter there is little point in attempting to reach, for example, pH 0. It will be apparent to one of ordinary skill in the art what sort of maximal variation is useful.

The identification of at least two parameters which can be varied widely in order to assure a wide range of binding affinities for the panel will depend on the chemical nature of the candidate paralogs in the panel, as will be further described below. While such parameters as hydrophobic moment and corrugation factor can readily be calculated for candidate peptides, panels of nucleic acids, for example, may vary in the number and spacing of homopolymeric regions and in symmetry indices. Derivatized polysaccharides may vary in branching and charge distribution. In all cases, the candidate panel is made up of individual paralogs which are maximally diverse over at least two such parameters, thus leading to a set with superabundant diversity. This is in contrast to prior art approaches where either only one parameter is varied (as is the case with supports for chromatography which vary only in hydrophobicity, or is the case of ampholyte supports which vary only in pI) or which have undefined variabilities over a very small range (such as is the case for the cyclodextrin based chromatographic supports or for affinity matrices based on textile dyes). For example, there are commercially available kits marketed by ICN for empirical choice of chromatographic supports useful in protein separation which are based on a series of affinity ligands representing analogs of Cibacron dyes. These dyes vary in properties over a very narrow range. The invention panels, in contrast, provide a range of diversity over an electron configuration and charge contour map as defined by at least two specific parameters. As is further described below, this can be achieved either by the design of the panel based on systematic variation of two or more parameters or may be achieved by screening a randomly generated panel against a complementary, maximally diverse, counter-panel which had been achieved through systematic two parameter variation design.

One set of polymers which is extremely convenient from the standpoint of synthesis is comprised of peptides since the nature of amino acyl residues, both naturally-occurring encoded residues, and others, provides a range of properties which is very easily incorporated in a systematic manner into the synthesis of a group of polymeric sequences. Such peptides can, of course, be modified to vary the nature of the linkage so that they may be considered "pseudopeptides" by converting the amide linkages to alternate forms using generally recognized means. Specifically, the peptide linkages can be replaced with other types of linkages such as $—CH_2NH—$, $—CH_2S—$, $—CH_2—$, $—CH{=}CH—$ (cis and trans), $—COCH_2—$, $—CH(OH)CH_2—$, and $—CH_2SO—$, by methods known in the art. The following references describe preparation of peptide analogs which include these alternative-linking moieties: Spatola, A. F., Vega Data (March 1983), Vol. 1, Issue 3, "Peptide Backbone Modifications" (general review); Spatola, A. F. in "Chemistry and Biochemistry of Amino Acids Peptides and Proteins", B. Weinstein, eds., Marcel Dekker, N.Y., p. 267 (1983) (general review); Morley, J. S. *Trends Pharm Sci* (1980) pp. 463-468 (general review); Hudson, D. et al *Int J Pept Prot Res* (1979) 14:177-185 ($—CH_2NHY—$, $—CH_2CH_2—$); Spatola A. F. et al, *Life Sci* (1986) 38:1243-1249 ($—CH_2—S$); Hann, M. M. J Chem Soc Perkin Trans I (1982) 307-314 (—CH—CH—, cis and trans); Almquist, R. G., et al, *J Med Chem* (1980) 23:1392-1398 ($—COCH_2—$); Jennings-White, C. et al *Tetrahedron Lett* (1982) 23:2533 ($—COCH_2—$); Szelke, M. et al, European Appln EP 45665 (1982) CA: 97:39405 (1982) ($—CH(OH)CH_2—$); Holladay, M. W. et al *Tetrahedron Lett* (1983) 24:4401-4404 ($—CH(OH)CH_2—$); and Hruby, V. J. *Life Sci* (1982) 31189-199 ($—CH_2—S—$). Particularly preferred is $—CH_2NH—$.

The peptides themselves can be synthesized chemically by means well known in the art such as, e.g., solid-phase peptide synthesis. The synthesis is commenced from the carboxy-terminal end of the peptide using an alpha-amino protected amino acid. t-Butyloxycarbonyl (Boc) protective groups can be used for all amino groups even though other protective groups are suitable. For example, Boc-protected C-terminal residues can be esterified to chloromethylated polystyrene resin supports. The polystyrene resin support is preferably a copolymer of styrene with about 0.5 to.2% divinyl benzene as a crosslinking agent which causes the polystyrene polymer to be completely insoluble in certain organic solvents. See Stewart, et al, *Solid-Phase Peptide Synthesis* (1969) W. H. Freeman Co., San Francisco and Merrifield, *J Am Chem Soc* (1963) 85:2149-2154. These and other methods of peptide synthesis are also exemplified by U.S. Pat. Nos. 3,862,925, 3,842,067, 3,972,859, and 4,105,602.

The synthesis may use manual techniques or automatically employ, for example, an Applied BioSystems 430A Peptide Synthesizer (Foster City, Calif.) or a Biosearch SAM II automatic peptide synthesizer (Biosearch, Inc. San Rafael, California), following the instructions provided in the instruction manual supplied by the manufacturer.

Alternatively, peptide paralogs can be produced by expression of recombinant DNA constructs prepared in accordance with well-known methods. Such production can be desirable to provide large quantities or by using mixtures of encoding DNAs, multiple embodiments of such paralogs. Since the peptide sequences are relatively short, recombinant production is facilitated.

Cyclic forms of the peptides can also be obtained using generally known methods. For chromatographic applications, it is advantageous to attach the linear compound to the solid support before conducting the cyclization reaction to promote intramolecular (as opposed to intermolecular) bonding. Disulfide linkages are formed by reacting peptides containing cysteine or cysteine analog residues with reagents which result in the formation of disulfide bonds, such as, for example, mildly oxidizing conditions. Esters and amides involving the sidechains of amino acids can be obtained synthetically by a suitable protection/deprotection protocol. It is understood that the requirements for deprotection vary with the protecting group; F-moc is released by the organic base piperidine, however, sidechain protecting groups are generally protected with groups which are stable to base, but labile to dilute trifluoroacetic acid (TFA). Another commonly used protecting group t-Boc is released by TFA, but alternative sidechain protecting groups can be used which are labile only to stronger conditions of treatment, with hydrogen fluoride, for example. Thus, the protecting agents can be removed from the groups whose interaction forms the backbone chain while sidechain carboxyl, amino, and hydroxyl groups such as the amino group of lysine, the carboxyl of aspartic acid, and the hydroxyl of threonine are protected by groups stable to the deprotection involved in the peptide synthesis. After the peptide is synthesized, deprotection of these groups in amino acids spaced 3-4 residues apart in the peptide chain, for example, followed by treatment with a standard peptide bond forming reagent such as dicyclohexylcarbodiimide (DCC) results in an internal loop of these 3-4 amino acids. Cyclic forms of the peptides which mimic paratopes or which otherwise exhibit specific binding may also be obtained by controlling the 3-dimensional conformation through the use of "molecular sticks" as described in U.S. patent application Ser. No. 172,633, assigned to the same assignee and incorporated herein by reference. Also, crosslinking may be effected using homo- or heterobifunctional linkers such as those available from Pierce Chemical Co., Rockford, Ill.

In an additional modification of peptide paralogs, the individual amino acid residues may be separated by peptide-type moieties which introduce conformational restraints. For example, "amino acyl" monomers of the formulas

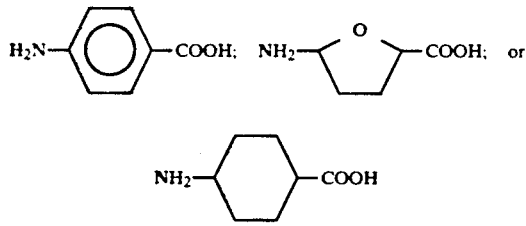

can be used between "normal" amino acyl residues in the synthesis of the peptides.

The choice of parameters for which maximal variation is to be obtained depends upon the nature of the paralog. For paralogs which are peptides, or compounds related to peptides such as peptides with altered linkages and/or their cyclized forms described above, at least five such parameters are useful candidates for variation. Two of these parameters are largely independent of conformation—the hydrophobic index and isoelectric point. Three of them are conformation-dependent and include the hydrophobic moment (a measure of the amphipathicity of the peptide or the extent of asymmetry in the distribution of polar and nonpolar residues); the lateral dipole moment, a measure of asymmetry in the distribution of charge); and a corrugation factor (defined by the inventors herein, which measures the variation in surface contour—for example, the scatter and the distribution of bulky sidechains along the helical backbone). These parameters will be discussed in turn.

The isoelectric point, pI, has its conventional meaning and, as is well known, refers to the pH at which the molecule referred to is electrically neutral. The pI can be altered to higher values by increasing the number of basic amino acids, such as lysine, arginine or histidine, which are positively charged at neutral pH. The pI can be shifted toward lower values by increasing the relative numbers of acidic amino acid such as aspartic acid or glutamic acid which are negatively charged at neutral pH. Intermediate pI values can be achieved by balancing the positive and negatively charged groups or by using uncharged amino acyl residues. Although gene-encoded amino acids have been used for ease of reference it is, of course, understood that any suitable amino acyl residue can be used, whether encoded by the gene or not, whether naturally-occurring or not, and whether in the D or L or meso form.

A discussion of the hydrophobic index as related to structure can be found in Eisenberg, D. R. M. et al *Faraday Symp Chem Soc* (1982) 17:109–120 and in Janin, J., *Nature* (1979) 277:491–492. Of course, the index can be varied toward hydrophobicity by increasing the number of hydrophobic residues such as phenylalanine, valine, isoleucine, etc. Shifts toward a lower hydrophobic index can be effected by use of hydrophilic or charged amino acids. The hydrophobic moment is determined by the amphipathic quality of the peptide, which can be varied by adjusting the periodic hydrophobicity of the residues (Eisenberg, D., et al *Proc Natl Acad Sci USA* (1984) 81:140–144; Eisenberg, D., et al Nature (1982) 299:371–374). The amphipathic property resides in the secondary or tertiary conformation of the peptide, resulting in portions or faces of the molecule which are water soluble and others which are hydrophobic. By taking account of conformation and the properties of the residues, this parameter can be readily adjusted. The lateral dipole moment is a reflection of the charge pattern due to the presence and placement of positive or negatively charged amino acid residues. The corrugation factor reflects the distribution of bulk and its effect on surface contours.

In more detail, the hydrophobic index (hi) is the sum over the amino acids in the peptide of the individual hydrophobic indices of the amino acid components. This can be formulated for a peptide of n amino acids by the formula:

$$hi(\text{peptide}) = \sum_{i=1}^{n} (hi)_i$$

The conformation-dependent parameters can be calculated by similar approaches which are, in each case, the modulus of the Fourier transform of the appropriate property function—i.e., the strength of the component of periodicity of period--delta, where "delta" is defined to match an alpha-helix (100°), or a beta sheet (170°). The assignment of the proper delta value will depend on the conformation normally assumed by the peptide, or that into which it is controlled by the designer of the peptide.

It is recognized, however, that the general relationships of the resulting parameters among members of a set do not appreciably change regardless of the assumptions made about the conformation. Thus, if the above parameters are calculated for all members of the set assuming, for example, an alpha-helix conformation, the resulting diversity in pattern will not vary appreciably even if the peptides in fact are not in the form of alphahelices. This result is particularly important in regard to very short peptides of insufficient length to attain a recognized, ordered conformation.

Therefore, the calculations of the three parameters, hydrophobic moment (hm), dipole moment (dm), and corrugation factor (cf) are as follows:

$$\mu(\delta) = \left\{ \left[ \sum_{n=1}^{N} H_n \sin(\delta n) \right]^2 + \left[ \sum_{n=1}^{N} H_n \cos(\delta n) \right]^2 \right\}^{\frac{1}{2}} =$$

$$\left| \sum_{n=1}^{N} H_n e^{i\delta n} \right|$$

wherein for hm, H=hi; for dm, H=overall charge at pH 7; and for cf, H=volume.

The values of the characteristics of individual amino acids which are required to calculate the values of the characteristics of the encoded amino acids which are in turn needed to calculate these parameters as described above are given in Table 1.

TABLE 1

| | | hydrophobic index | pka | chg pH 7 | volume (A³) | Rel freq |
|---|---|---|---|---|---|---|
| Ala | A | 0.25 | X | 0 | 91.5 | 6 |
| Asp | D | −0.72 | 3.86 | −1 | 124.5 | 6 |
| Glu | E | −0.62 | 4.25 | −1 | 155.1 | 6 |
| Phe | F | 0.61 | X | 0 | 203.4 | 4 |
| Gly | G | 0.16 | X | 0 | 66.4 | 7 |
| His | H | −0.40 | 6.0 | +0.1 | 167.3 | 3 |
| Ile | I | 0.73 | X | 0 | 168.8 | 4 |
| Lys | K | −1.10 | 10.53 | +1 | 171.3 | 7 |
| Leu | L | 0.53 | X | 0 | 167.9 | 7 |
| Met | M | 0.26 | X | 0 | 170.8 | 2 |
| Asn | N | −0.64 | X | •0 | 135.2 | 4 |
| Pro | P | −0.07 | X | 0 | 129.3 | 5 |
| Gln | Q | −0.69 | X | 0 | 161.1 | 4 |
| Arg | R | −1.76 | 12.48 | +1 | 210.9 | 4 |
| Ser | S | −0.26 | X | 0 | 99.1 | 8 |
| Thr | T | −0.18 | X | 0 | 122.1 | 6 |
| Val | V | 0.54 | X | 0 | 141.7 | 6 |
| Trp | W | 0.37 | X | 0 | 237.6 | 2 |
| Tyr | Y | 0.02 | 10.07 | 0 | 203.6 | 3 |

An initial candidate panel can consist of about 90-100 peptides or related compounds for convenience. This is entirely a reflection of the design of commercially available microtiter plates and protein synthesizer rods (Cambridge Research Biochemicals) and is a convenient number to provide sufficient individual tests to frame the characteristics of the desired paralog. The synthesis is conducted using conventional, usually commercially available, methods.

A number of paradigms can be used to design the set having maximal diversity in the chosen parameters. In one protocol, the first formulated paralog, for example, will have each position filled by randomly chosen amino acids. The next candidate, also constructed by a random selection, will be compared to the first candidate for differences in the two or more measured and calculated parameters. Depending on whether there are substantial differences in these parameters, this candidate peptide will be retained or discarded. As more and more candidates are tested, of course, the greater is the likelihood that the candidate will have properties too close to one already in the set to warrant retention, and the larger number of candidates that will need to be formulated and screened before the member is retained in the set. The process will continue until the number of candidates examined since the last one was accepted becomes unacceptable. In general, the pattern expected is as shown below:

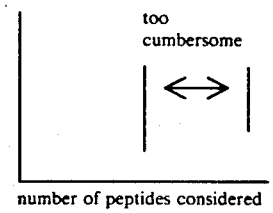

where the formulation and selection process should cease somewhere in the indicated region.

In order to obtain a final panel of 48, it is preferred to provide initially approximately 96 diverse candidates to permit final fine tuning by hand. For example, the dipole moments of the sidechains as compared to the dipole moment of the backbone might be considered. The final panel should be reviewed so that a distribution of properties exists for all varied parameters—i.e., each peptide differs from all others by at least X% (after normalization of the scale to the range of 0–100 units), the value of X being determined by the "cumbersome" zone on the graph. Thus, each peptide is substantially different from all other peptides in the set with regard to at least one of the two or more parameters. This approach is advantageous because computation is easier than synthesis. Full diversity is however, to some extent undermined due to thermally induced fluctuations in conformation.

The results of a computerized reduction to practice of this approach for preparation of a diverse set of 30 peptides averaging 6 amino acids is shown in FIG. 1. In this example, all five parameters were evaluated. The program creates random peptide sequences for which the five parameters are calculated wherein those with properties similar to the previously generated sequences are discarded. After trial runs to establish extreme values for each parameter, all five ranges were divided into three parts, thereby defining 35 ° r 243 unique combinations of properties ("bins"). From the first about 200 random sequences of 6 mers proposed, 50 bins out of the 243 were filled. Filling the next 50 then required examining about 2,000 more sequences and additional thousands then contributed only about a dozen new combinations. With independent sets of randomly generated sequences, it was found that the same subset of bins was filled, implying that not all combinations are physically attainable with these monomers, for example a peptide cannot be both hydrophobic and highly charged.

As shown in FIG. 1, variations in isoelectric point and hydrophobicity are plotted along the X and Y axis respectively. The symbols within the field represent the conformation-dependent parameters measuring distribution of hydrophobic, bulky, and charged constituents according to X=high, squiggle=medium, and 0=low. This figure, thus, shows that a random set is conveniently designed.

As stated above, with respect to computerized design or otherwise systematic design, it is recognized that there are certain combinations of parameters that may not be possible—for example, the same paralog cannot easily be both highly charged and highly hydrophobic. It was found that only a modest number of peptides are needed to provide good coverage of all the known properties relevant to binding, described above. This is in agreement with previous work which has shown that considerable variability in the natural amino acid sequence is possible with little binding effect on interaction of antibodies with peptides. Lerner, R. A. *Nature* (1982) 299:592-596; Geysen, H. M. et al *Proc Natl Acad Sci USA* (1984) 81:3998-4002.

Final selection of the peptide or other paralog panel is generally done manually to improve the evenness of sampling of the accessible portion of, for example, the 5-dimensional peptide space.

Another approach to the preparation of diverse panels is analogous to that used for the preparation of ampholytes for isoelectric focusing. To prepare these ampholytes, dextrans are derivatized by conjugation to charged functional groups, typically sulfonates to provide negative charges and amino functionalities to provide positive charges. A random distribution of derivatization is produced in the reaction. The resulting ampholytes are then sorted by isolelectric focusing to provide supports with a range of a single parameter—pI. For application to the invention herein, in this alternate approach, the compounds are randomly synthesized polymers which are then isolated by their ability to bind to a maximally diverse set of candidate paralogs which has been prepared by the designed systematic variation of at least two parameters. Thus, once an initial or model diverse paralog panel is designed, for example, as described above using peptides or their related compounds as the candidate panel moieties, the diversity of this panel can be used to segregate mixtures of other materials, including nonpeptide composite polymers, into a diverse set by specific binding of the members of the random mixture to each candidate peptide in the model paralog panel. This permits the synthesis of panels with superabundant diversity even for polymers which can be randomly varied by variation in the monomer units, but for which analytical appreciation of the specific two parameters associated with their chemical types is difficult.

It has been noted above that the paralogs need not be constructed of peptides or their close relatives. Additional embodiments which permit variability of at least two measures of properties analogous to those set forth above for peptides can also be used. The only requirement is that the paralogs be constructed of variable parts so that their properties can be systematically varied. For example, nucleic acid sequences are known to have different specific binding properties with respect to various proteins. Indeed, it is understood that the regulation of gene expression occurs by virtue of these specifically-binding proteins which have a specific affinity for particular sequences in the genetic material (see, for example, Tjian, R. et al *Science* (1989)245:371-378). While many of the parameters associated with peptide variability, such as pI and hydrophobicity index are difficult to vary in this case, other parameters such as GC/AT ratio are conveniently made to fall into values over a range. In addition to overall GC/AT ratio, the placement and variation of GC and AT on a single strand, the number and placement of homopolymeric stretches (such as AAAA and GGGG), and the nature and placement of symmetric regions in the strands can also be varied. In the case of symmetric regions, it is known that those which represent dyad-type symmetry—for example GATXATC (commonly misidentified as palindromic sequences) are known to permit formation of intrachain loops due to base pairing, and are also prominent among sites recognized by dimeric proteins, including several restriction enzymes. True palindromes such as GATTAG have different effects on properties. In any case, the foregoing provides a number of parameters, any two of which can be maximally varied to produce the paralog panels of the invention. As nucleic acids are readily synthesized, use of these polymeric compounds as candidate paralogs has considerable advantage. Also, because it is known that specific nucleic acid/protein interactions occur, randomly constructed nucleic acid mixtures could be segregated by binding to individual members of the diverse peptide panel described above.

Methods for constructing nucleic acid polymers of predetermined and arbitrary sequences are well established. While appropriate DNA fragments could, in principle, be isolated from natural sources and utilized in accordance with the methods of the invention, it is clearly preferable to design and synthesize nucleic acid sequences with the required diversity of properties de novo. Commercially available methods include solid phase-based synthesis of DNA fragments of more than sufficient length to represent the paralogs of the invention.

A similar approach is convenient in preparing alternate paralog forms such as those formed by copolymers of hydrophilic and hydrophobic components such as combinations of polyethylene and polyethylene glycol subunits. Alternate hydrophilic/hydrophobic or even potentially charged monomeric units such as methacrylic acid can be used in these constructs. For example, copolymers of PEG and polyvinyl chloride or of methacrylic acid and propylene, and the like can be formed, and then segregated into maximally diverse embodiments.

Similarly, carbohydrates can be derivatized with charged groups such as sulfates and amines at various random levels and segregated according to their diverse properties; even phosphodiglycerides can be constructed which have a variety of properties.

It is thus a function of the invention to provide panels of maximum diversity which can then be subjected to screening procedures to obtain the most desired paralog for the application at hand. The panels can be packaged into kits for conduct of the screening procedures. A further description of such kits follows the description of the screening method which is set forth below.

SCREENING PROCEDURES

In one approach, the procedure to screen the panels for the most advantageous candidate paralog can be used repeatedly because the binding-based assays used to detect specific affinity are generally reversible so that the testing compositions can subsequently be removed from the paralog panel which remains bound to solid supports. It is not necessary to perform such assays in a recoverable form or bound to solid supports, but it is highly convenient to do so.

The reusability is particularly convenient in the context of one of the intended uses of the paralog—as an affinity ligand in chromatography, since the relative binding strengths in a series of proposed elution solvent systems can be tested systematically. For example, the strength of binding in a series of solutions containing methanol at increasing concentrations or solutions at increasing salt concentrations simulating elution gradients can be used. In this type of testing the comparative behavior of a number of paralogs under a multitude of elution conditions can be tested empirically. This may be very helpful in that the binding constant gradient obtained for paralog X may be preferable to that obtained for paralog Y under desired elution conditions even though paralog Y might appear to have a preferable specific affinity level when tested under only one solvent or temperature condition. The reusability of the test panel thus permits the selection of the best paralog under a pattern of conditions which simulates its use in the chromatographic procedure.

Figure 2:
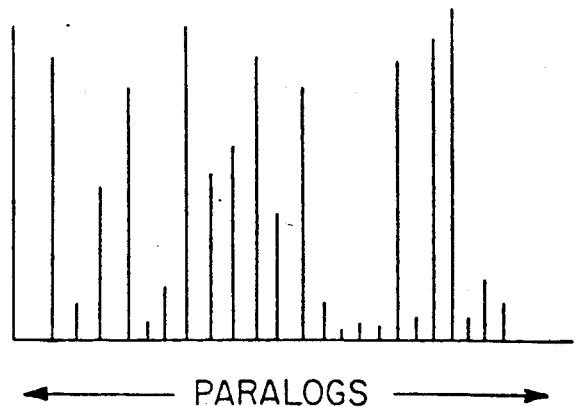
FIG. 2 shows the generic results of a typical ELISA binding assay wherein a panel of paralogs is reacted with a single labeled analyte.

However the panel is formulated for testing, the panel is then tested for specific affinity of its members to the selected moiety. On a theoretical basis, one might do this directly by labeling the moiety and detecting the relative amount of label bound to the individual paralog members of the panel. Using this approach, a pattern similar to that shown in FIG. 2 will be obtained. As shown in FIG. 2, the amount of label bound to each member of the panel (the y coordinate) is shown across the members of the panel (the x coordinate). Varying amounts of labeling are obtained, depending on the affinity of each paralog for the moiety. "Labels" such as enzymatic activity or other detectable property of the moiety can also be used.

An alternative to this direct method is sometimes more practical. In this alternative, specific affinity is assayed by means of competition of the unlabeled moiety with a mixture of labeled peptides or other suitable ligands. The mixture must contain a sufficient number of members so that more or less equivalent binding to all paralogs by the labeled mixture per se in the absence of moiety is obtained. This general approach for detecting binding of an unlabeled substance to members of a panel is described in more detail in copending application U.S. Ser. No. 108,130, filed 13 October 1987 and assigned to the same assignee and incorporated herein by reference.

Briefly, the mixture of the requisite number of random ligands (roughly on the order of 500-1000, although in some instances smaller members may suffice) is labeled in a suitable manner, for example, in the case of peptides, using the acyl iodination method with the iodine isotope 125 as described by Bolton, A. E., et al, *Biochem J* (1973) 529-539, and available commercially from ICN Radiochemicals. The mixture can be prepared directly by synthesis of individual members and mixing them together or, more conveniently, can be obtained by hydrolysis of large proteins or other polymers into random small peptides or other oligamers. One approach, for example, utilizes a partial trypsin hydrolysate (Cleveland, D. W., et al *J Biol Chem* (1977) 252:1102-1106) of a yeast lysate. This provides a large number of peptides which can be labeled as a mixture, or which can be separated using, for example, SDS gel electrophoresis and transferred to a test support such as Immunodyne (Burnette, W. N. *Anal Biochem* (1981) 112:195-203 if their binding is to be assessed individually.

Figure 3:
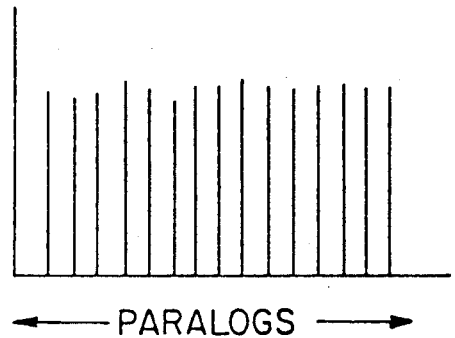
FIG. 3 shows the generic results of a typical ELISA binding assay wherein a panel of paralogs is reacted with a mixture of labeled peptides.

It may be necessary in utilizing the labeled ligand mixture to verify that satisfactory binding occurs with regard to all candidate paralogs in the panel. The conditions for effecting this equivalent binding throughout the panel should also be established empirically. In a perfect situation, the ligand mixture will bind uniformly to all panel members as shown in FIG. 3A. However, more frequently, only similar levels of binding are found, as in FIG. 3B. This provides a perfectly workable basis for competition with analyte. Interpretation of results when competition is added can be simplified by normalization of the binding values to the same value before evaluating the competition.

Figure 4:
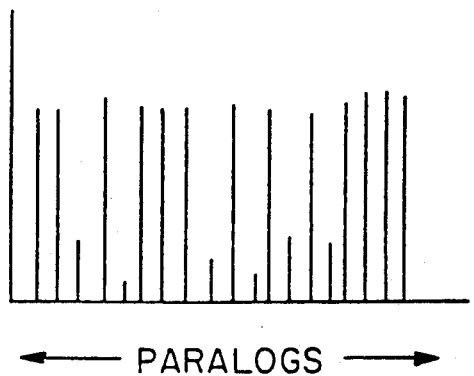
FIG. 4 shows the generic results of the corresponding assay of the same paralog panel with the labeled mixture in the presence of unlabeled analyte.

When it is confirmed that the labeled ligand mixture binds roughly equivalently to all candidate paralogs in the absence of selected moiety, or similar binding has been normalized, the screen is repeated in the presence of the desired moiety, such as an analyte. Those candidates which have specific affinity for this moiety will show a decrease in the conjugation to labeled ligand mixture, the decrease being proportional to the specific affinity of the candidate for the moiety. A typical competition pattern is shown in FIG. 4. The meaning of the coordinates is the same as in the other figures. The paralogs with greatest affinity to the selected moiety, however, show the lowest levels of labeling as this indicates successful competition of the selected moiety with the labeled ligand mixture for the paralog. By assessing the ability of the moiety to compete, those paralogs which show the greatest decrease in label uptake are selected as having the parameters that are most favorable for binding selected moiety.

The screening process can be repeated with additional panels having properties intermediate to those members which show the greatest specific affinity or the most desirable elution pattern behavior in the original panel, in order to fine-tune the molecular shape and charge distribution pattern of the ultimately chosen paralog. The screen can be repeated an arbitrary number of times with an arbitrary number of panels to the degree of specific affinity or the chromatographic behavior required. The electron cloud pattern of the paralog panel can thus be systematically manipulated to optimize the affinity of the paralog for the selected moiety; if the paralog will be used as an affinity ligand in a chromatographic procedure, an affinity that is so great that elution is difficult may not be desirable, and the correct pattern should be chosen. The effect of conformation control can also be studied, as described above.

Figure 5:
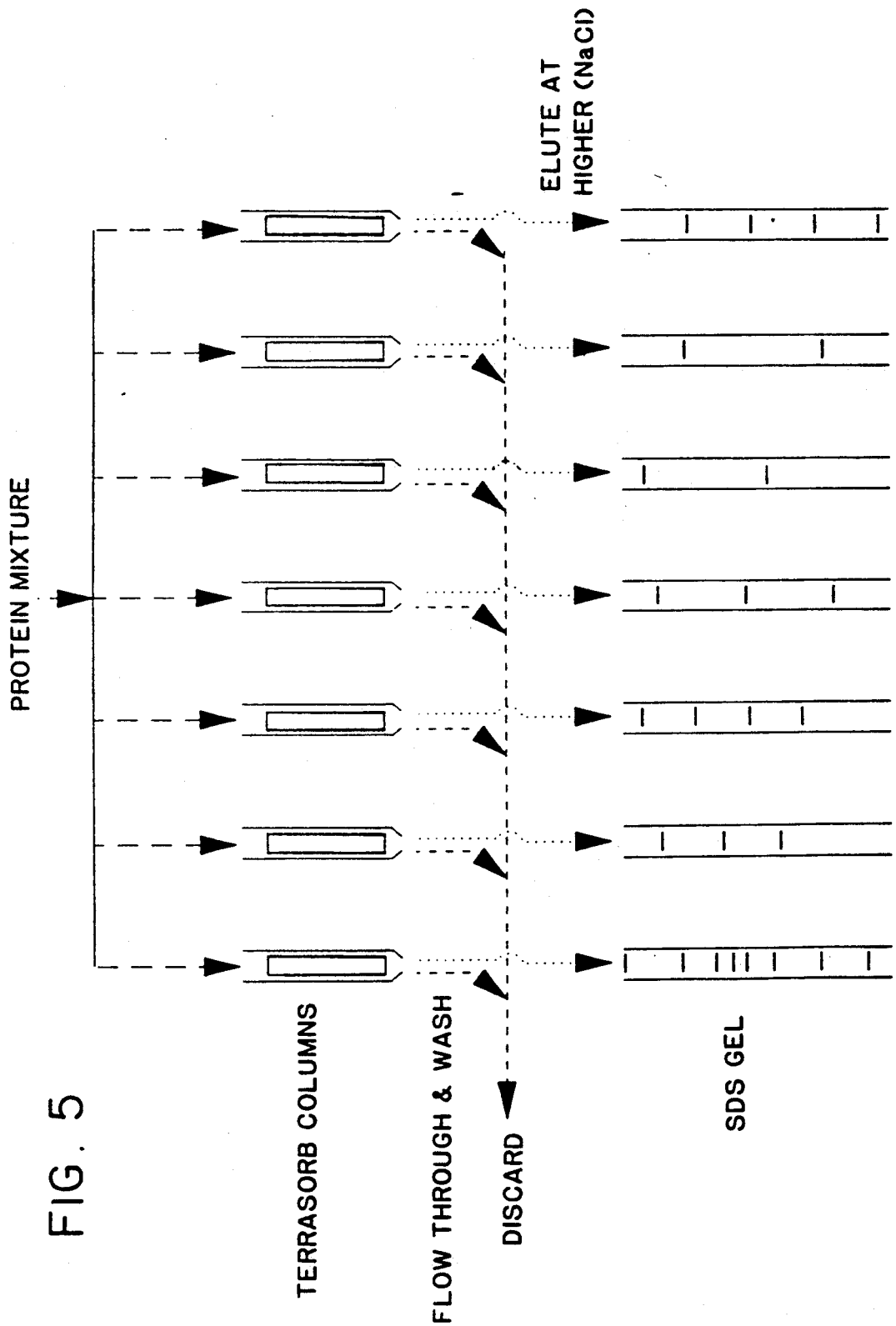
FIG. 5 shows a schematic of a chromatographic kit to determine proper paralog ligands for separation of a desired mixture.

In an alternative embodiment, the paralogs can be packaged in a manner intended to simulate their intended use by conjugation to solid supports which are then packaged as chromatographic minicolumns as shown schematically in FIG. 5. A desired number of columns representing diverse candidate paralogs are then contacted with the protein or other mixture containing the desired analyte. The flowthrough volume is discarded and the columns are then eluted with a suitable elution solvent, such as concentrated salt. The eluates are then examined for the presence or absence of the desired analyte.

In the representation shown in FIG. 5, the eluates are subjected to analysis by SDS-PAGE to determine the pattern of analyte adsorption from a protein mixture. As shown in the figure, the diverse paralog set is able to adsorb and elute different proteins from a complex mixture employed as a test sample.

Figure 6:
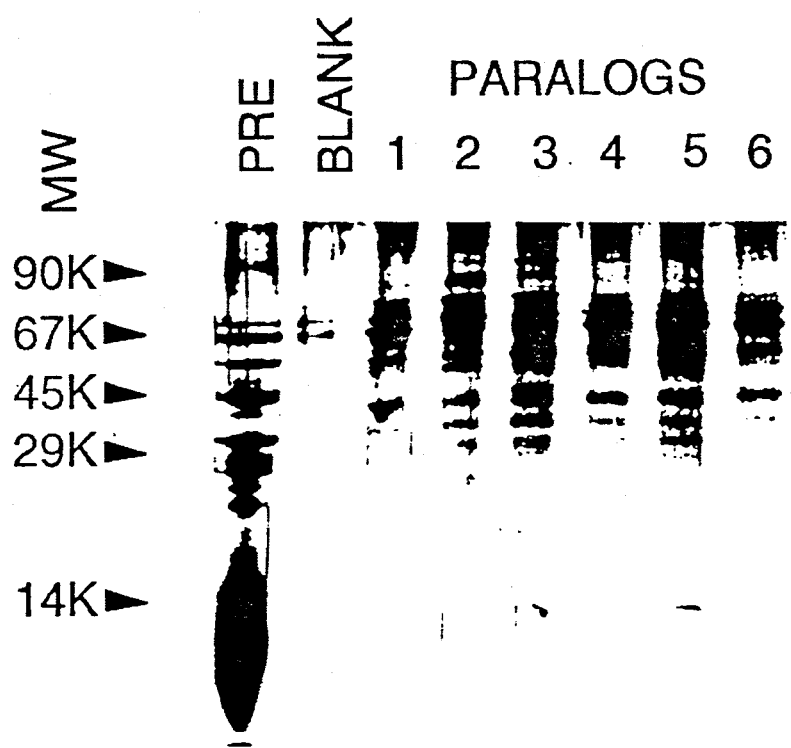
FIG. 6 shows the results of application of a yeast lysate to a series of six paralog columns.

The results of this approach as applied to a yeast hydrolysate and a series of six paralog columns is shown in FIG. 6. In this illustrative experiment, a total cell lysate of yeast (Sigma Y-2875) was partially purified on DEAE cellulose and the portion binding to DEAE cellulose between 50 and 150 mM NaCl was isolated and dialyzed against 10 mM Tris HCl buffer, pH 7.5, at 10 mg/ml. A sample of 100 ul was applied to a series of 0.15 ml bed volumes in minicolumns filled with Affigel (BioRad) derivatized with 2 umoles paralog per ml settled bed volume. After unbound proteins were washed through, the columns were eluted with 250 mM NaCl and the pattern of bound proteins analyzed by SDS gel-electrophoresis.

Lane 1 of FIG. 6 shows the pattern obtained from the material loaded onto the columns; lane 2 shows the results of elution of the mixture when underivatized support was used as the column; virtually no proteins were eluted, and the electrophoresis gel shows the common doublet silver stain artifact at 65 kd. This artifact is believed to be due to a combination of the ubiquitous keratin protein and oxidized dithiothreitol. The results of the remaining six lanes 3–8 indicate that different proteins are adsorbed and eluted from different paralogs.

Other configurations for test panels can, of course, also be used. For example, membrane-bottomed microtiter plates are available commercially from Pall Corporation. These microtiter plates contain membranes at the bottom of the wells which are capable of supporting a settled bed of solid support. The membranes do not pass fluid unless a pressure differential is applied by vacuum or by centrifugation. Thus, the sorbents of the wells can be tested as pseudochromatographic columns by applying the appropriate solutions and then passaging the solutions through the column by creating the required pressure gradient.

USE OF THE SELECTED PARALOGS

When a paralog of suitable specific affinity for a selected moiety is found according to the method of the invention, the application of the selected paralog is appropriate wherever such specific affinity is required. In addition to utility as a specifically binding ligand on a chromatographic support for separation of an analyte from contaminants, the ability of the paralog specifically to bind the selected moiety may be employed by using the paralog as a specific binding reagent in an assay, analogous to an immunoassay, which depends on this specific interaction. In addition, if the selected moiety is a receptor or other biological target, the paralog will be useful in a variety of pharmacological and therapeutic applications.

For use in chromatography, when a paralog with satisfactory characteristics for a desired analyte is chosen, it is conjugated to a solid support using conventional means known in the art. Typical solid supports include polysaccharide supports, acrylamide gels, silica supports, alumina, and the like across the range of typical commercially available chromatography supports. It should be noted that in addition to particulate chromatographic supports, membrane type supports are also commonly used. A number of chromatographic membranes are available commercially. A wide variety of conjugation techniques is also available including those which introduce a linking arm, if desired, between the solid support and the paralog ligand. The use of a linking arm of a length equivalent to at least 3–9 carbons is advantageous in some instances in order to provide greater accessibility of the analyte to the ligand.

The resulting substrate, comprising solid support (particulate or membrane) conjugated to a paralog specific for binding to the desired analyte, can then be used in a manner conventional for chromatographic substrates. Particulate supports can be packed into columns or placed in filter beds to adsorb the analyte when the composition containing the analyte is contacted with the substrate. Since the paralog is a relatively stable ligand, preparations and columns packed with the invention substrate can be included in apparatus designed for HPLC.

The advantages of adapting affinity-based chromatography to HPLC cannot be easily overestimated, especially if the chromatographic procedure is conducted on a preparative scale. Resolution in preparative procedures needs to be achieved on the basis of the characteristics of the column rather than the brute force methods of increasing the size of the column or adjusting the strength of the eluant downward so that elution will take a longer time period. Any adjustment which increases the complexity or amount of eluting solvent is a serious drawback on a preparative scale. For example, expensive solvents and complex mixing protocols are reasonable when a total of 10–100 ml is required as in analytical procedures; they become expensive and problematical when hundreds of gallons are required as is often the case in preparative protocols. Not only does the solvent need to be recovered in order to lower the cost, an expensive process in itself, but it also needs to be removed from the product being prepared.

In addition, since material purified by preparative chromatography is generally required to be recycled through the column to effect adequate resolution, complex elution protocols have the additional disadvantage of requiring reequilibration of the column in the recycled phase. Faster reequilibration is also advantageous for analytical separations done in large numbers as is the case for most industrial applications.

For the foregoing reasons, in general, analytical procedures become scaleable only when the basis for the separation is selectivity of the absorbent—i.e., is based on an affinity chromatography approach.

In one particularly preferred protocol, a column can be constructed having a series of paralogs of varying, generally increasing, affinity for the target analyte. The succession of binding affinities as the analyte travels through the column is effective in improving resolution. In a typical embodiment, the column begins with a paralog ligand which has very low affinity for the target; the paralogs to follow have increasing affinity.

Accordingly, columns packed with substrate having paralog ligands can be used as either analytical or preparative tools, and the use of paralog-derivatized substrate columns provides a convenient and efficient alternative to more conventional chromatographic approaches. If the analyte is a drug, the paralog-derivatized substrate can be used as a specific reagent to adsorb the drug from body fluids and the drug can then be recovered for analysis. If the analyte is a toxin appearing in waste products, the substrate can be used for detection, and also for removal of the toxin from the mixture. If the analyte is a desired product made in low yield, the substrate can be used to isolate the product batchwise or using standard chromatographic techniques.

It might also be noted that, as for the most part paralogs are chiral molecules, paralog-based columns may be employed for the direct separation of an enantiomeric mixture and other chiral preparations.

Advantage can also be taken of those paralogs which have the property of specific affinity for toxins by using them as scavengers in vitro and in vivo. For example, in one embodiment, latex beads conjugated to paralog might be delivered to the intestines or the bloodstream as an antidote to poisoning or used in more conventional extracorporeal applications. In another embodiment, such configurations might be used as delivery systems for drugs which bind specifically, but with moderate affinity to the paralog, particularly in cases where the paralog-drug combination provides properties which permit taking advantage of the ability of the paralog to bind receptors associated with physiological transport, such as cases wherein the drug must cross the blood-brain barrier or enter solid tumor tissues.

As stated above while the selected paralog has utility when conjugated to solid support, especially in chromatography, the utility of the paralog is not limited to its solid-bound form. The paralog of appropriate composition and characteristics can also be used to substitute for the corresponding antibody or fragment thereof in standard immunoassays. For use in this manner, the paralog may or may not be labeled, depending on the protocol. For example, in a typical sandwich assay, microtiter wells coated with paralog are used to test samples for antigen, wherein antigen bound to paralog is then labeled using the labeled form antibody specific for a different epitope or with the labeled form of an alternate paralog Or, labeled paralog can be used to compete with any analyte antibody in a sample for antigen bound to solid substrate. As is well understood in the art, the variety of specific protocols for solid phase-based and agglutination-based immunoassays is vast and well understood by practitioners of the art.

The following examples are intended to illustrate but not to limit the invention.

EXAMPLE 1

Design of a Paralog Panel

Figure 8:
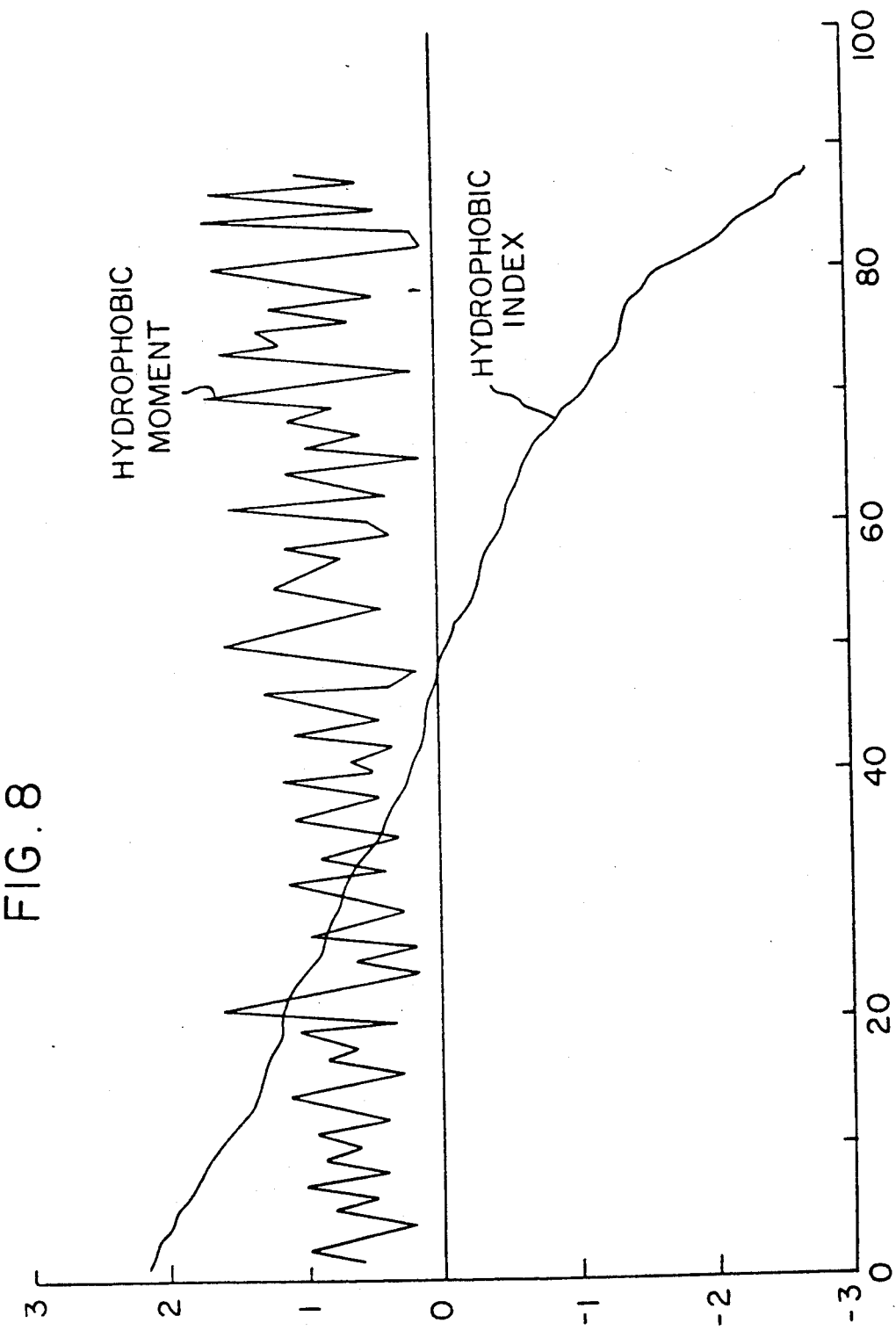
FIG. 8 shows the variation in hydrophobicity index and hydrophobic moment across the panel of FIG. 4.

A panel of 88 pentapeptides is designed on the basis of decreasing hydrophobicity and periodic variation of hydrophobic moment. FIG. 7 shows the list of pentapeptides synthesized numbered 1-88, along with 8 additional controls for use in synthesis according to the method of Geysen, H. M., et al, *Proc Natl Acad Sci USA* (1984) (supra); FIG. 8 shows the hydrophobic index and the hydrophobic moments across this panel.

The panel is synthesized using the commercial version of Geysen's technique (Cambridge Research Biochemicals) or any other convenient multiple peptide synthesis format. The panel is then probed with a protein for which a label is available, and the pattern of binding established. When a reasonable number of successful candidate paralogs has been obtained, these successful candidate paralogs are synthesized using routine peptide synthesis methods in sufficient quantity to verify their sequence and perform additional chromatographic experiments. The peptide is linked to the solid support Affi-gel 10 (Bio-Rad) and packed into a column, or the chromatographic support is obtained by allowing the peptide to remain on the silica-based support Ultra-Affinity ™ (Beckman) upon which it was synthesized.

In order to verify that the paralog has the required specific affinity, a similar column can be prepared using a scrambled form of the paralog's amino acid sequence as ligand. The analyte will bind to the paralog-containing column, but not to the scrambled peptide-containing one. The Atassi references (supra) confirm that such scrambling destroys binding.

EXAMPLE 2

Cyclization of Paralogs

A. Three paralogs of dissimilar properties, KNRGFK, KGYLYLYK and GKUIUIUK (where U=para amino benzoic acid), each containing available lysine residues, are attached, at pH 6.5, through their N-terminal amino groups to Baker-bond CBX beads previously derivatized with N-hydroxysuccinimide. After coupling, the lysine residues are intramolecularly joined using the homobifunctional cross-linking reagent difluoro-dinitro-benzene. A color change is used to monitor the reaction (single point reaction with the cross-linker yields a faint yellow color; full cross-linking yields a dark yellow color). The beads are packed into a standard stainless steel chromatography column using a slurry packer.

B. Cyclization alters the properties of a paralog by two major mechanisms. First, it reduces the conformational freedom of the backbone, and second, it creates a partial cavity into which analytes may insert. FIG. 9 shows chromatograms of the hydrophobic analyte insecticide DDD on columns prepared as in paragraph A after cyclization, along with controls using underivatized CBX sorbent and NHS-derivatized CBX blocked with ethanolamine. As shown in the figure, the DDD peak is progressively later eluted from the supports: blocked CBX, cyclized GKUIUIUK, cyclized KGYLYLYK and cyclized KNRGFK.

EXAMPLE 3

Design of a Diverse DNA Panel

FIG. 10 shows an illustration of a computer program designed to generate nucleic acids of diverse values of four properties: total G/C percent; number of G/C regions; level of direct symmetry; and level of complementary strand (dyad) symmetry. For each property, the low value was assigned the value of 1 and a high value was assigned a value of 2. By use of the program, the results of which are shown in FIG. 10, a 16-member panel with maximum diversity in these four properties was designed. As shown in the figure, for each 20-mer synthesized, the first line gives the sequence generated and the successive four lines gave parameters used in calculating the property descriptors. The bin number is characterized by the pattern of 1 and 2 designations of the four properties; the actual values of the properties associated with these designations are shown in the next line.

The 20-mers thus designed are then synthesized using standard solid-phase techniques for coupling to suitable supports and construction of the paralog panel.

I claim:

1. A method to identify a paralog useful for the conduct of affinity chromatography with respect to an analyte which has specific affinity for a first moiety in comparison to additional moieties present in the environment of the first moiety which method comprises:
   screening, for ability to selectively bind said first moiety a panel of individual candidate paralogs, wherein said candidate paralogs have systematically varied values of at least two different parameters, each of which parameters determines the ability of the paralog to bind other substances.

2. The method of claim 1 wherein the candidate paralogs of said panel have systematically varied values of at least 3 parameters.

3. The method of claim 2 wherein the candidate peptides of said panel have systematically varied values of at least 4 parameters.

4. The method of claim 3 wherein the candidate peptides of said panel have systematically varied values of at least 5 parameters.

5. The method of claim 1 wherein said parameters are selected from the group consisting of hydrophobic index, isoelectric point, hydrophobic moment, lateral dipole moment, and corrugation factor.

6. The method of claim 1 wherein the candidate paralogs are peptides of at least 4 amino acid residues, wherein said peptides may optionally contain modification of one or more peptide linkage to replace said linkage with a linkage selected from the group consisting of —CH$_2$NH—, —CH$_2$S—, —CH$_2$CH$_2$—, —CH=CH— (cis and trans), —COCH$_2$—, —CH(OH)CH$_2$—, and —CH$_2$SO—.

7. The method of claim 6 wherein said paralogs contain 5-15 amino acids.

8. The method of claim 6 wherein said parameters are selected from the group consisting of hydrophobic index, isoelectric point, hydrophobic moment, lateral dipole moment, and corrugation factor.

9. The method of claim 1 wherein said candidate paralogs are nucleic acids.

10. The method of claim 9 wherein said parameters are selected from the group consisting of AT/GC ratio, placement of AT and GC on a single strand, number and placement of homopolymeric stretches, dyad asymmetry and palindromic asymmetry.

11. The method of claim 1 wherein said candidate paralogs are cyclic peptides of at least 4 amino acid residues, wherein said peptides may optionally contain modification of one or more peptide linkage to replace said linkage with a linkage selected from the group consisting of —CH$_2$NH—, —CH$_2$S—, —CH$_2$CH$_2$—, —CH=CH— (cis and trans), —COCH$_2$—, —CH(OH)CH$_2$—, and —CH$_2$SO—.

12. The method of claim 11 wherein said cyclic paralogs are cyclized by formation of a covalent bond selected from the group consisting of a disulfide, an ester, and an amide.

13. The method of claim 11 wherein said cyclic paralogs are formed using a bifunctional linker.

14. The method of claim 1 wherein said candidate paralogs are synthetic polymers comprised of hydrophilic and hydrophobic monomer units.

15. The method of claim 14 wherein said hydrophobic monomer units provide ethylene chloride residues and said hydrophilic monomeric units provide ethylene glycol residues.

16. The method of claim 1 wherein said candidate paralogs are carbohydrates derivatized with positively and negatively charged groups.

17. The method of claim 16 wherein said carbohydrate is dextran, and said charged groups are sulfate and amino groups.

18. The method of claim 1 wherein said candidate paralogs are phosphatidyl diglycerides.

19. The method of claim 1 wherein said candidate paralogs are peptides containing at least one residue selected from the group consisting of para-amino benzoic acid, para-amino cyclohexyl carboxylate, and 1-carboxy-4-aminofuran.

20. The method of claim 1 wherein said screening step is conducted by assessing the ability of said first moiety to compete with a labeled mixture, which mixture is capable of binding to all candidate paralogs in the panel, for binding to each candidate paralog in the panel.

21. The method of claim 1 wherein said screening is conducted by passaging sample containing said first moiety through a multiplicity of test portions, each test portion containing a candidate paralog attached to solid support, under conditions wherein specifically binding materials will be adsorbed, eluting any adsorbed materials, and detecting the presence or absence of said first moiety in the unbound or eluted material, to determine whether said first moiety shows specific binding to said candidate paralog attached to solid support.

22. The method of claim 21 wherein said test portions are minichromatographic columns.

23. The method of claim 21 wherein said test portions are contained in a membrane-bottomed microtiter plate.

24. The method of claim 1 wherein said screening is conducted by individually testing each candidate paralog for ability to bind said first moiety.

25. The method of claim 1 wherein said panel is prepared by synthesizing individual candidate paralogs according to predetermined values for said parameters over the range of values of said parameters.

26. The method of claim 1 wherein said panel is prepared by synthesizing a random mixture of said candidate paralogs and sorting said paralogs for ability to bind to a series of ligands, which ligands have systematically varied values of at least two said parameters which determine the ability of the ligand to bind to other substances.

27. A method to identify a paralog useful for the conduct of affinity chromatography with respect to an analyte in a sample containing additional components, wherein said paralog has specific affinity for said analyte in comparison to said additional components, which method comprises:

screening, for ability to selectively bind said analyte, a panel of individual candidate paralogs, wherein said candidate paralogs have systematically varied values of at least two parameters, each of which parameters determines the ability of the paralog to bind other substances.

28. The method of claim 27 wherein said screening is conducted by passaging sample containing said analyte through a multiplicity of test portions, each test portion containing a candidate paralog attached to solid support, under conditions wherein specifically binding materials will be adsorbed, eluting any adsorbed materials, and detecting the presence or absence of said analyte in the unbound or eluted material to determine whether said analyte shows specific binding to said candidate paralog attached to solid support.

29. The method of claim 28 wherein said test portions are minichromatographic columns.

30. The method of claim 28 wherein said test portions are contained in a membrane-bottomed microtiter plate.

* * * * *